United States Patent
Roane

Patent Number: 5,586,886
Date of Patent: Dec. 24, 1996

[54] ROTARY HANDPIECE FOR ENDODONTIC INSTRUMENTS

[76] Inventor: James B. Roane, 707 SW. 24th St., Suite 201, Norman, Okla. 73069

[21] Appl. No.: 520,992

[22] Filed: Aug. 30, 1995

[51] Int. Cl.⁶ ............... A61C 5/02; A61C 1/10; A61C 3/00
[52] U.S. Cl. ............ 433/224; 433/102; 433/114
[58] Field of Search ............... 433/72, 114, 116, 433/102, 122, 123, 224

[56] References Cited

U.S. PATENT DOCUMENTS

| | | | |
|---|---|---|---|
| 1,694,857 | 12/1928 | Kulik | 433/102 X |
| 3,578,745 | 5/1971 | Garnier | 32/57 |
| 3,713,221 | 1/1973 | Malmin | 433/102 X |
| 3,969,823 | 7/1976 | Nakanishi | 32/27 |
| 4,243,388 | 1/1981 | Arai | 433/27 |
| 4,443,193 | 4/1984 | Roane | 433/102 |
| 4,629,426 | 12/1986 | Levy | 433/118 |
| 4,940,410 | 7/1990 | Apap et al. | 433/102 |

FOREIGN PATENT DOCUMENTS

| | | | |
|---|---|---|---|
| 207037 | 6/1959 | Australia | 433/102 |
| 2616652 | 12/1988 | France | 433/224 |
| 497996 | 5/1930 | Germany | 433/102 |

OTHER PUBLICATIONS

Nakanishi Dental Mfg. Co., Ltd. *Clinical & Laboratory Rotary Cutting Instruments*, pp. 4–9, printed in Australia, Dec. 21, 1993.

*Primary Examiner*—Nicholas D. Lucchesi
*Attorney, Agent, or Firm*—Dougherty, Hessin, Beavers & Gilbert

[57] ABSTRACT

The present invention provides an improved rotary handpiece for cleaning and enlarging the root canal of a tooth with a rotary endodontic file. The handpiece includes a retractable support rod attached to and extending from the handpiece positioned adjacent and substantially parallel to the endodontic file. The support rod is adapted to rest on a tooth whereby the retraction of the support rod controls the advance of the endodontic file into the root canal. The control of the advance of the endodontic file insures that the file does not self thread into the canal or become excessively loaded whereby it sticks or breaks off while the root canal is being cleaned and enlarged.

20 Claims, 3 Drawing Sheets

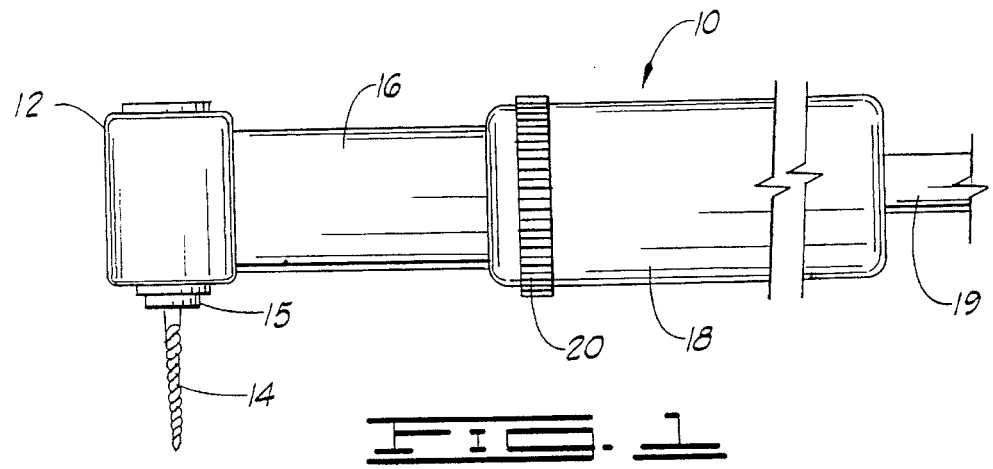
FIG. 1
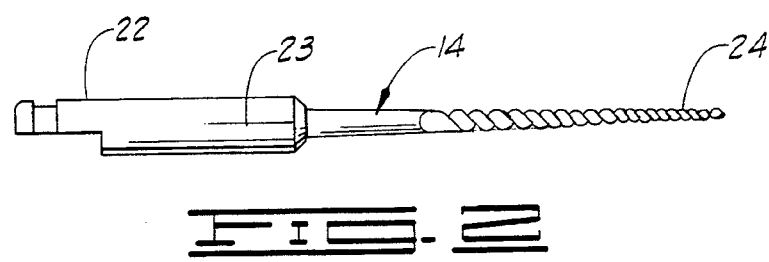
FIG. 2
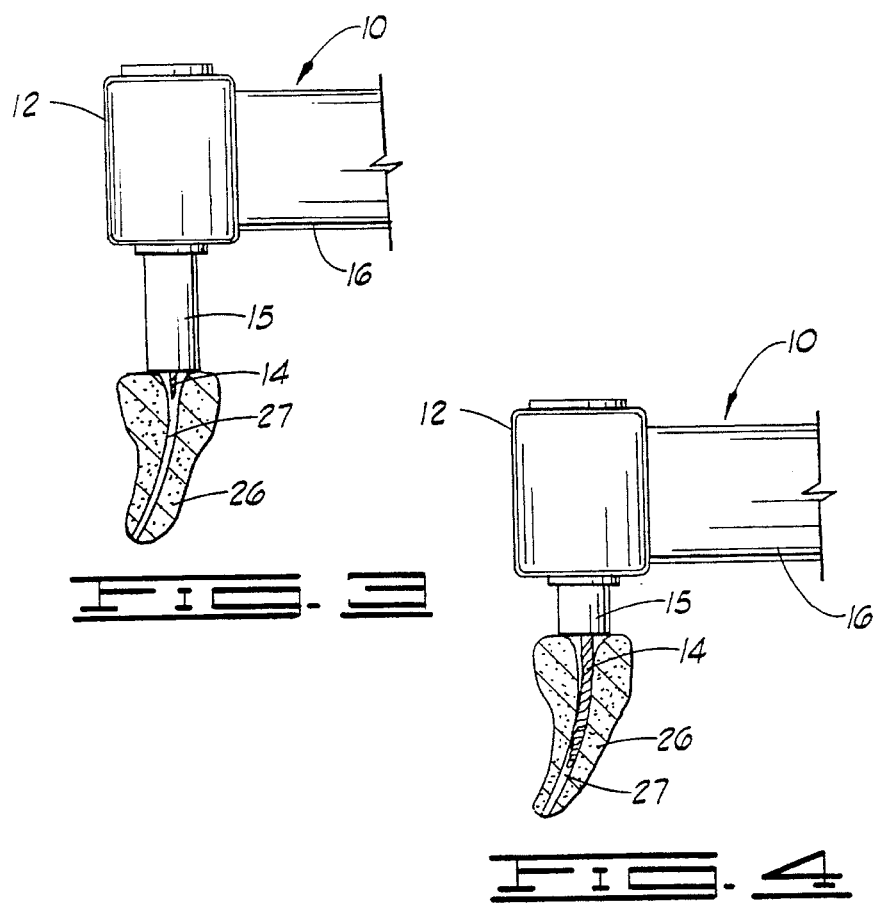
FIG. 3
FIG. 4

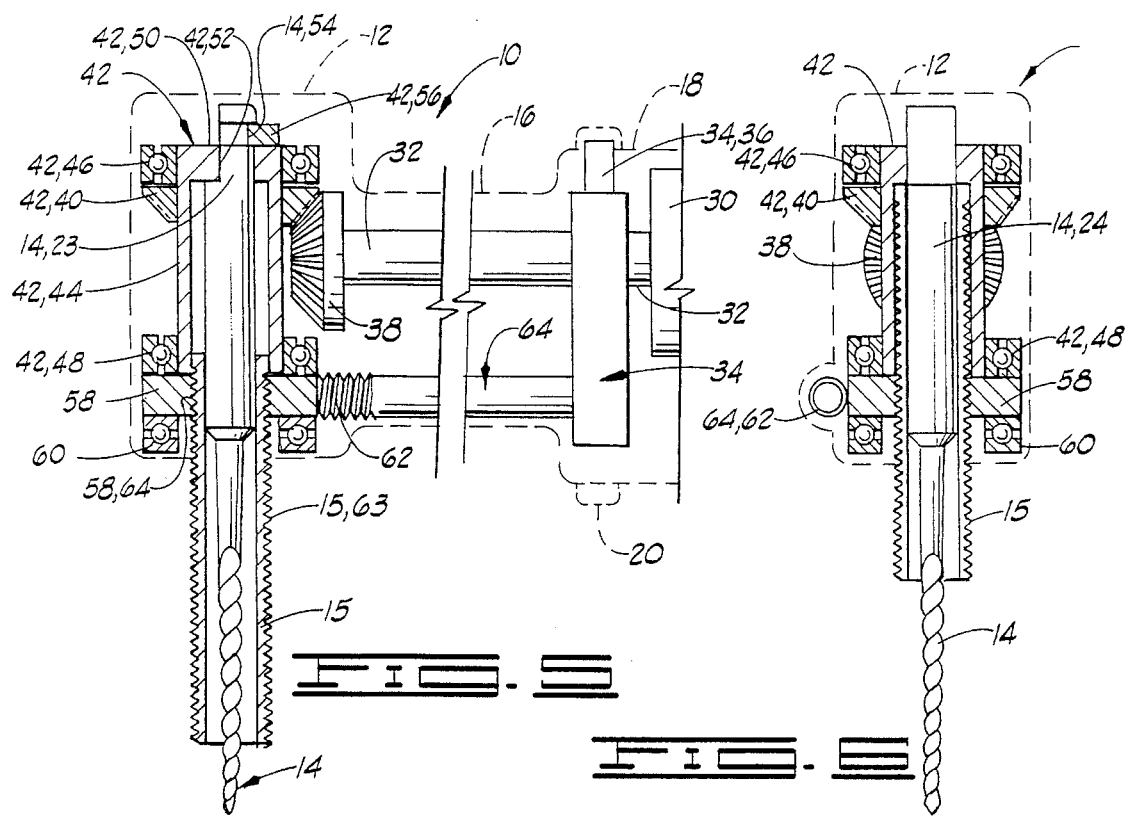
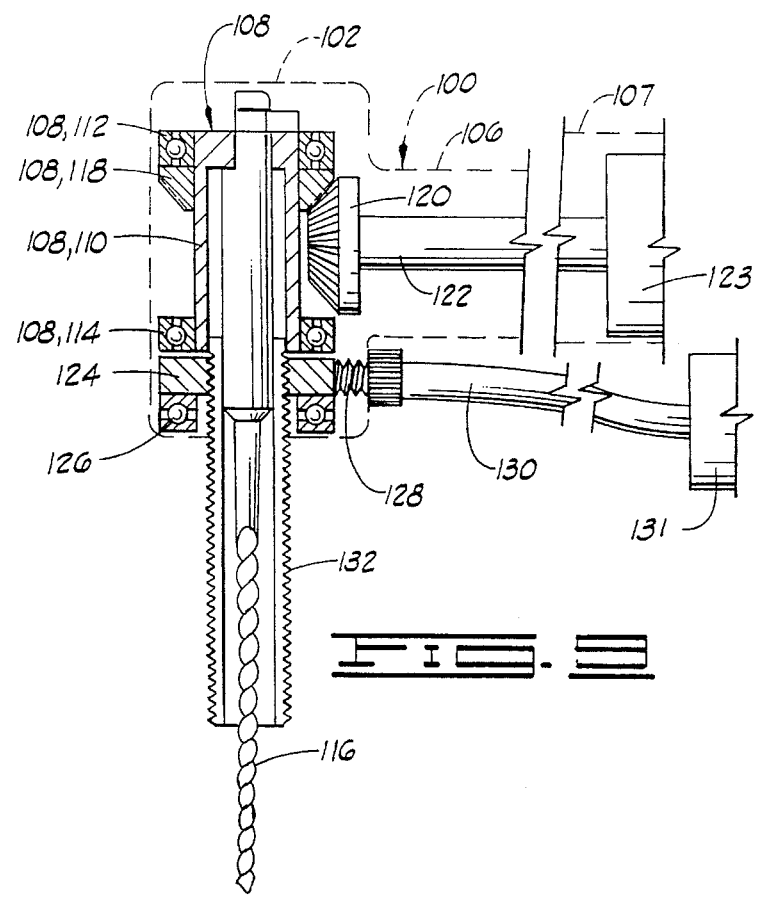

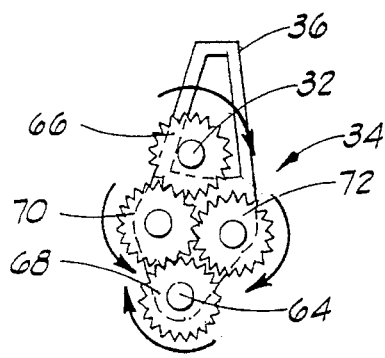
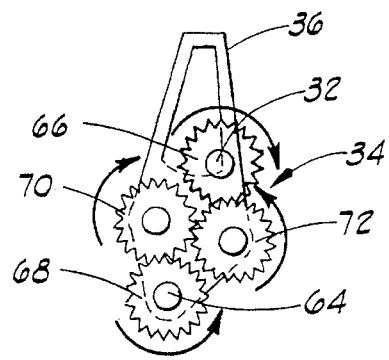
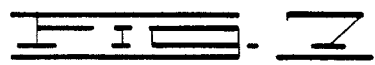
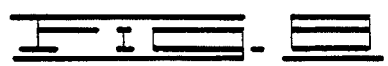
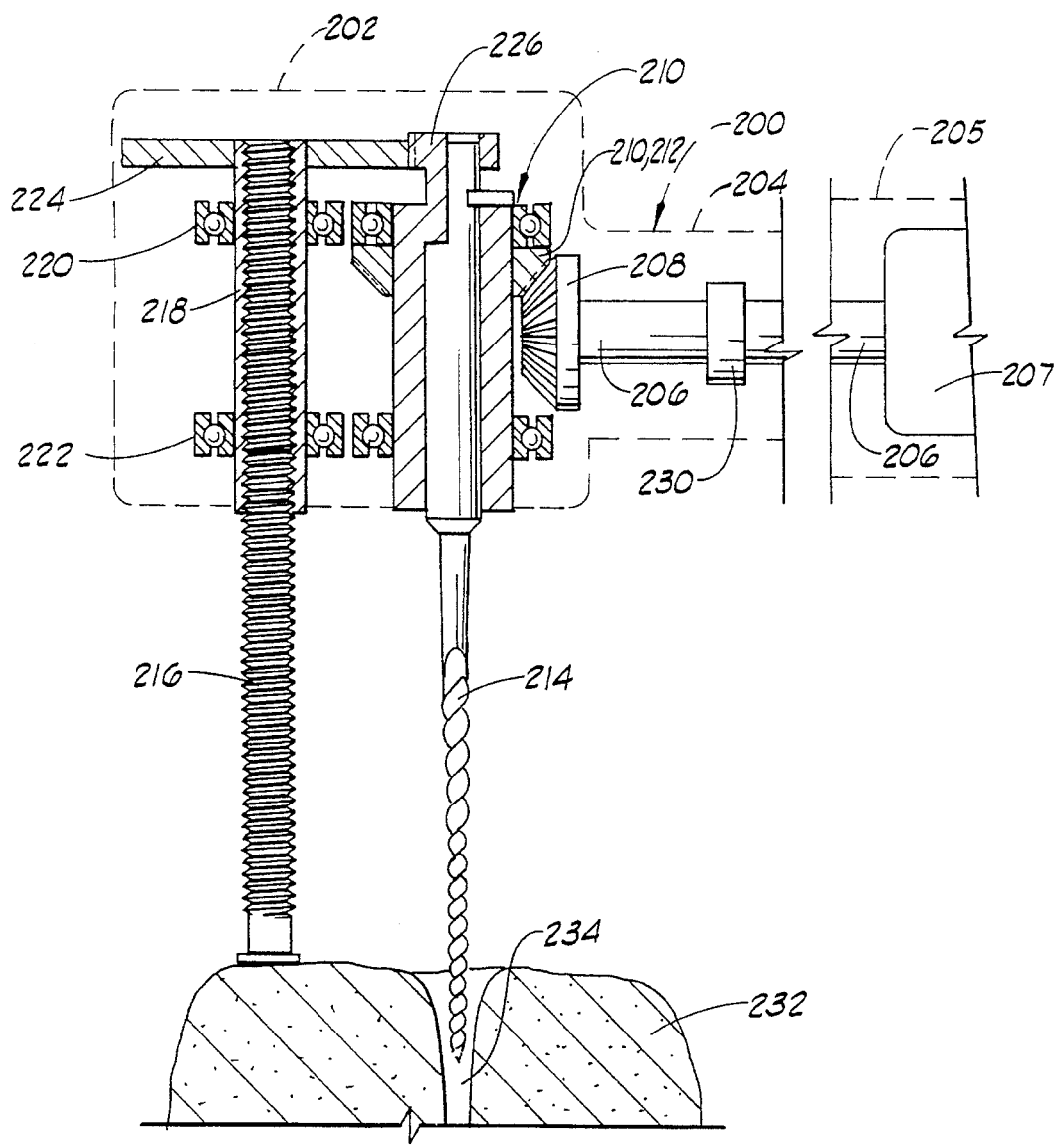

5,586,886

ROTARY HANDPIECE FOR ENDODONTIC INSTRUMENTS

BACKGROUND OF THE INVENTION

1. Field of the Invention

The present invention relates to a rotary handpiece for endodontic files used to clean and enlarge root canals of teeth.

2. Description of the Prior Art

Endodontics is the branch of dentistry which involves the treatment of pulp through root canal therapy. Such therapy generally involves the cleaning of the root canal to remove damaged tissue therefrom and to enlarge the root canal so that it can be filled with an inert sealing material, e.g., gutta-percha. Typically, a dentist will drill into the upper part of the tooth to locate the root canal and thereafter clean and enlarge the root canal using small endodontic instruments, generally referred to in the art as "files."

The cleaning and enlarging of a root canal is complicated by the fact that the root canal is not only very small but often follows a curved path. Accordingly, the file must be very thin and flexible in order to enter the root canal and follow its path. Also, the file must have a sufficient strength so that it is not easily broken off within the root canal.

Heretofore, the most common procedure followed by dentists in performing root canals has been to utilize hand manipulated endodontic files of progressively increasing size. A particularly effective such endodontic file is known as a K-type file which includes a tapered shaft having a conical point and three or four spiral cutting edges along the length of the tapered portion of the shaft. When a K-type file is manipulated by hand to clean and enlarge a root canal, a number of types of cutting strokes can be utilized which generally fall into the categories of filing or reaming. A filing stroke utilizes axial reciprocation of the cutting instrument along the length of the root canal without rotating the instrument. Thus, the edges of a K-type instrument cut the interior walls of the root canal when a filing stroke is used therewith. A reaming stroke refers to the use of rotational motion established by rotating the instrument about its longitudinal axis. While there are various kinds of instruments, some of which cut in a single rotational direction, K-type files have spiral cutting edges which are rotationally bi-directional in that they may cut when rotated either clockwise or counterclockwise. The spiral cutting edges are generally right handed whereby when a K-type file is rotated clockwise, it tends to thread itself into the root canal like a wood screw. Thus, the dentist must be careful not to penetrate too deeply into the root canal as a result of self-threading which can damage the tooth and subject the file to excessive loading whereby it sticks or breaks off in the canal.

A variety of dental instrument drive devices, known in the art as "handpieces", have been developed for rotating dental instruments. While the use of rotary handpiece driven endodontic files has achieved some degree of success, a continuing problem involves the self threading of the endodontic instrument into the canal whereby the instrument progresses into the canal too rapidly and becomes excessively loaded. Such excessive stress on the instrument driven by a handpiece can result in sticking or breaking of the instrument in the canal, a condition which is difficult to correct.

Thus, there is a need for an improved rotary handpiece for cleaning and enlarging a root canal of a tooth with a rotary endodontic file which prevents the file from becoming excessively loaded due to self threading and the problems which result therefrom.

SUMMARY OF THE INVENTION

The present invention provides improved rotary handpieces and methods of cleaning and enlarging a root canal of a tooth utilizing a rotary endodontic file. The improved handpiece of the invention basically comprises a rotary drive which rotates a chuck for holding and rotating an endodontic file. A retractable support rod is attached to and extends from the handpiece positioned adjacent and substantially parallel to the endodontic file. The support rod is adapted to rest on a tooth whereby the retraction of the support rod controls the advance of the endodontic file into a root canal. Means are attached to the handpiece and to the support rod for retracting the support rod and advancing the endodontic file at a controlled rate into the root canal whereby the endodontic file does not become excessively loaded while the root canal is being cleaned and enlarged.

The methods of the invention for cleaning and enlarging a root canal of a tooth utilizing a rotary endodontic file basically comprise the first step of connecting the endodontic file to a handpiece of this invention having a retractable support rod connected thereto. The handpiece is then positioned with the endodontic file positioned to enter a root canal and the support rod resting on a tooth. The endodontic file is rotated at a speed sufficient to clean and enlarge the root canal when the file is advanced into the root canal by the retracting support rod. The retraction of the support rod and advance of the rotating endodontic file into the root canal are controlled at a rate whereby the endodontic file does not become excessively loaded while the root canal is being cleaned and enlarged.

It is, therefore, a principal object of the present invention to provide improved rotary handpieces and methods for cleaning and enlarging the root canals of teeth with rotary endodontic files.

Other and further objects, features and advantages of the present invention will be readily apparent to those skilled in the art upon a reading of the description of preferred embodiments which follows.

BRIEF DESCRIPTION OF THE DRAWINGS

FIG. 1 is a side view of the forward part of a rotary handpiece of the present invention having an endodontic file attached thereto.

FIG. 2 is an enlarged side view of the endodontic instrument of FIG. 1.

FIG. 3 is a side view of the forward most part of the handpiece of FIG. 1 with the endodontic instrument inserted into the root canal of a tooth and with a retractable support rod which is a part of the handpiece extended therefrom.

FIG. 4 is a side view similar to FIG. 3 illustrating the handpiece after the retractable support rod has been retracted at a controlled rate whereby the endodontic file while being rotated was advanced into the root canal at the same controlled rate.

FIG. 5 is an enlarged partly sectional side view illustrating the internal parts of the rotary handpiece of FIG. 1.

FIG. 6 is a partially sectional front view of the internal parts of the handpiece of FIG. 5.

FIG. 7 is a schematic illustration of the reversing transmission illustrated in FIG. 5 in a first position.

FIG. 8 is a schematic illustration of the reversing transmission of FIG. 7 in a second position.

FIG. 9 is an enlarged partly sectional side view of the internal parts of an alternate embodiment of the rotary handpiece of the present invention.

FIG. 10 is an enlarged partly sectional side view of the internal parts of another alternate embodiment of the rotary handpiece of the present invention positioned on a tooth.

DESCRIPTION OF THE PREFERRED EMBODIMENTS

In my U.S. Pat. No. 4,443,193 issued Apr. 17, 1984, an improved K-type endodontic file is described. The improved file includes a plurality of spiral rotationally bi-directional cutting edges and a non-ledging tapered tip shaped such that the sharp cutting points which are normally present in a K-type file at the intersections between the ends of the cutting edges and a standard 75° (plus or minus 15°) included angle conically tapered tip are substantially eliminated.

By eliminating the .sharp points, the high stress concentration previously created when the points engage tooth material in a curved root canal is eliminated. That is, the forces exerted by the axially forward most part of the improved file against the wall of a curved root canal is spread over a much greater area of the tooth material and transportation of the instrument and ledging of the canal are eliminated or reduced.

Prior to the present invention, my improved K-type file and other endodontic files were most commonly hand manipulated to prevent self threading, excessive stress from force being exerted on the instruments and sticking or breaking of the instruments as was often the case when an endodontic instrument driven by a rotational handpiece was used.

Referring now to the drawings, and particularly to FIG. 1, the improved rotational handpiece of the present invention is illustrated and generally designated by the numeral 10. The handpiece 10 is basically comprised of a head portion 12 having an internal rotating chuck (not shown) for holding and rotating an endodontic file 14. The head portion 12 is connected by a shank portion 16 to a rotary drive portion 18 which causes the chuck to rotate. In addition, a retractable and extendable quill or support rod 15 is connected to the head portion 12 which functions to control the rate of advance of the endodontic file 14 into a root canal. The drive portion 18 can optionally include a switch 20 connected to a transmission for reversing the direction of movement of the support rod 15. A cable 19 containing a drive shaft, electric wires or conduits for delivering power to the drive portion 18 is attached thereto.

The retractable support rod 15 is positioned substantially parallel to the endodontic file 14 held by the rotatable chuck in the head portion 12. When the handpiece 10 is operated, the support rod 15 is extended, the file 14 is rotated at a predetermined speed and the support rod is retracted at a predetermined relatively slow rate to thereby control the advance of the endodontic file 14 into the root canal being cleaned and enlarged.

The drive mechanism within the drive portion 18 of the handpiece 10 can be mechanically, electrically, hydraulically or pneumatically operated. The cable 19 thus contains a rotatable drive shaft, electric wires or hydraulic or pneumatic conduits which connect to the drive mechanism within the drive portion 18.

An enlarged view of the endodontic file 14 is shown in FIG. 2. Preferably, the file 14 is a K-type file having a non-ledging tip of the type described in my previously mentioned '193 patent. Such files are commercially available under the trade names Flex-R® and Onyx-R® from the Union Broach Division of Moyco Industries, Inc. of York, Pa. The proximal end portion 22 of the file 14 includes an enlarged shaft portion 23 which is of a well known design for matingly engaging a quick release mechanism (not shown). The quick release mechanism is conventional and is a part of the internal rotatable chuck in the head portion 12 of the handpiece 10. The distal end portion 24 of the file 14 is inserted into the root canal to be cleaned and enlarged.

Referring now to FIGS. 3 and 4, in operation of the handpiece 10 and root canal cleaning file 14, the retractable support rod 15 of the head portion 12 is extended and placed on a tooth 26 with the distal end 24 of the file 14 positioned to enter a root canal 27 of the tooth 26. The drive mechanism of the handpiece 10 is started whereby the file 14 is rotated (generally in a clockwise direction) at a predetermined speed and the support rod 15 is retracted at a relatively slow rate. The retraction of the support rod 15 allows the rotating endodontic file 14 to enter the root canal 27 of the tooth 26 at a controlled rate (FIG. 4) whereby the file 14 does not self feed into the canal or become excessively loaded while the root canal is being cleaned and enlarged.

Referring now to FIGS. 5–8, the internal parts of the handpiece 10 are illustrated. As best shown in FIG. 5, the drive portion 18 of the handpiece 10 includes a drive motor 30 having a drive shaft 32 connected to a reversing transmission 34. The transmission 34 includes a shift lever 36 which engages the rotatable ring 20. The drive shaft 32 extends through the transmission 34 and through the shank portion 16 of the handpiece 10 to the head portion 12 thereof. A beveled gear 38 is attached to the drive shaft 32 within the head portion 12 and it engages a second beveled gear 40 which is a part of and attached to an endodontic instrument chuck assembly 42. The beveled gears 38 and 40 are arranged whereby the horizontal rotational motion of the shaft 32 is changed to a vertical rotational motion, i.e., the vertically positioned chuck assembly is caused to rotate.

The chuck assembly 42 is comprised of a cylindrical member 44 which is journaled within the head portion 12 of the handpiece 10 by bearings 46 and 48. The partially closed upper end portion 50 of the cylindrical member 44 includes a partially circular opening 52 for matingly engaging a complimentary portion of the enlarged shaft portion 23 of the endodontic file 14. The upper most part of the shaft portion 23 of the file 14 extends through the opening 52 and includes a horizontal slot 54 into which a movable latch member 56 extends. The chuck assembly 42 is conventional and is well understood by those skilled in the art as is the latch member 56 which is a part of a conventional quick release latching mechanism (not shown).

Positioned immediately below cylindrical member 44 of the chuck assembly 42 is a rotary gear member 58 journaled within the head portion 12 of the handpiece 10 by a bearing 60. The rotary gear member 58 is rotated by a worm gear portion 62 of a shaft 64 connected to the reversing transmission 34. Thus, when the shaft 64 is rotated, the rotary gear member 58 is also rotated, and when the direction of rotation of the shaft 64 is reversed by operation of the reversing transmission 34, the rotation of the rotary member 58 is also reversed.

In the form shown in FIGS. 5 and 6, the retractable support rod 15 is cylindrical and includes external threads 63 thereon. The support rod 15 extends through a central threaded opening 64 in the rotary gear member 58, and the threads 63 of the rod 15 are engaged by the threads in the threaded opening 64. Thus, when the rotary gear member 58 rotates in one direction, the support rod 15 is retracted within the cylindrical member 44 of the chuck assembly 42 as shown in FIG. 6. When the rotary gear member 58 is rotated in an opposite direction, the support rod 15 is extended as illustrated in FIG. 5.

Referring now to FIGS. 7 and 8, the reversing transmission 34 is schematically illustrated. The transmission 34 is conventional and is comprised of a gear 66 connected to the drive shaft 32 and a gear 68 connected to the shaft 64. A pair of gears 70 and 72 are journaled to the shift arm 36 between the gears 66 and 68. The gear 70 is positioned to always be engaged with the gear 68 and the gear 72 is positioned to always be engaged with the gear 70. When the shift arm 36 is moved, the gears 70 and 72 are moved to alternately engage the gear 66. Thus, when the shift arm 36 is moved to a first position as shown in FIG. 7, the gear 66 is engaged with the gear 70. When the shaft 32 and gear 66 are rotating clockwise and the gear 66 is engaged with the gear 70, the gear 70 rotates counterclockwise which causes the gear 68 and shaft 64 to be rotated clockwise. When the shift lever 36 is moved to a second position as shown in FIG. 8 whereby the gear 66 engages the gear 72 instead of the gear 70, the gear 72 is caused to rotate counterclockwise which in turn causes the gear 70 to rotate clockwise. The gear 70 engaged with the gear 68 causes the gear 68 to rotate counterclockwise which in turn rotates the shaft 64 counterclockwise. By moving the shift lever 36 between the positions shown in FIGS. 7 and 8, the shaft 64 is caused to selectively rotate clockwise (FIG. 7) or counterclockwise (FIG. 8). The reversing transmission can be placed in neutral by moving the shift arm 36 to a position whereby the gear 66 is disengaged from both the gears 70 and 72.

Thus, in operation of the handpiece 10 illustrated in FIGS. 5–8, the drive motor 30 is activated so that the chuck assembly 42 and the endodontic file 14 are rotated in a selected direction (generally clockwise) at a preselected speed, e.g., a speed in the range of from about 30 rpm to about 3000 rpm. The shift lever 36 of the reversing transmission is manipulated to cause the shaft 64 to rotate in the direction which extends the support rod 15 as shown in FIG. 5. With the reversing transmission in neutral, the support rod is positioned whereby it rests on a tooth with the endodontic file 14 positioned to enter the root canal to be cleaned and enlarged (FIG. 3). The shift lever is then manipulated to retract the support rod 15 into the head portion 12 of the handpiece 10 which advances the file 14 into the root canal (FIG. 4). The rate at which the support rod 15 is retracted is a rate such that the endodontic file 14 is advanced into the root canal at a corresponding rate which prevents the file 14 from self threading and becoming excessively loaded while moving through the root canal. Generally, the rate at which the support rod is retracted and the endodontic file is advanced is a rate in the range of from about 0.001 to about 0.1 millimeters per revolution of the endodontic file 14.

Referring now to FIG. 9 an alternate embodiment of the handpiece of the present invention is illustrated and generally designated by the numeral 100. The handpiece 100 is similar to the handpiece 10 and includes a head portion 102, a shank portion 106 and a drive portion 107. A chuck assembly 108 is provided in the head portion 102 which is essentially the same as the chuck assembly 42 of the handpiece 10 in that it includes a cylindrical member 110 which is journaled within the head portion 102 of the handpiece 100 by bearings 112 and 114. An endodontic file 116 is latched within the cylinder 110 in the same manner as described above for the assembly 42 of the handpiece 10. A beveled gear 118 is attached to the cylindrical member 110 of the chuck assembly 108 which is engaged by a second beveled gear 120 attached to a drive shaft 122. The drive shaft 122 is connected to a rotary drive mechanism 123 of one of the types described above in connection with the handpiece 10.

Positioned immediately below the chuck assembly 108 is a rotary gear member 124 journaled within the head portion 102 of the handpiece 100 by a bearing 126. The rotary gear member 124 is rotated by a worm gear 128 which is attached to a second drive shaft or a shielded rotating cable 130. The drive shaft or shielded cable 130 is connected to a second rotary drive 131 which can be inside the hand piece 100 or outside the handpiece as shown in FIG. 9. A cylindrical retractable and extendable support rod 132 having external threads similar to the support rod 15 of the handpiece 10 is threadedly engaged within a central threaded opening in the rotary gear member 124. Thus, when the rotary gear member 124 is rotated by the worm gear 128, the support rod 132 is retracted or extended.

The operation of the handpiece 100 is identical to the operation of the handpiece 10 except that the retraction and extension of the support rod 132 is controlled independently of the rotation of the chuck assembly 108 and the endodontic file 116. That is, the second rotary drive 131 connected to the drive shaft or cable 130 can be manually started, stopped and reversed as required or the second drive 131 can be operated by an electronic control device such as a computer. When a computer is utilized, it can be programmed in advance of a root canal cleaning and enlarging operation to start and stop at appropriate times. For example, the advance of the endodontic file into the root canal can be periodically stopped so that the root canal can be irrigated. The advance can also be stopped when an instrument change is required with the support rod automatically being re-extended, etc. The computer can also be connected to the main drive of the handpiece 100 whereby the rotation of the file 116 as well as the movement of the support rod 132 are preprogrammed and automatically controlled.

Referring now to FIG. 10, yet another alternate embodiment of the handpiece of the present invention is illustrated and generally designated by the numeral 200. The handpiece 200 includes a head portion 202, a shank portion 204 and a drive portion 205. A rotary drive 207 within the drive portion 205 rotates a drive shaft 206 which has a beveled gear 208 connected thereto. The beveled gear 208 engages the beveled gear 212 of a chuck assembly 210. The chuck assembly 210 is substantially identical to the chuck assemblies 42 and 108 described above in connection with the handpieces 10 and 100. An endodontic file 214 is latched in the chuck assembly 210.

Instead of a cylindrical retractable support rod having the endodontic file 214 disposed therein, the handpiece 200 includes a solid support rod 216 which is positioned parallel to the axis of and adjacent to the file 214. As illustrated in FIG. 10, the support rod 216 is close to the file 214 whereby it can rest on a surface of a tooth which is close to or contains the root canal which is to be cleaned and enlarged by the file 214. The support rod 216 includes external threads and is threadedly engaged within a cylindrical threaded member 218 which is journaled within the head portion 202 by a pair of bearings 220 and 222. A rotary gear 224 is connected to the top end of the threaded cylinder 218 which is engaged with a gear member 226 attached to and a part of the chuck assembly 210. Thus, when the chuck assembly 210 is rotated by the rotary drive 207 of the handpiece 200, the threaded cylindrical member 218 is also rotated at a fixed lower speed. A spring loaded friction clutch 230 is connected in the shaft 206 so that if the support rod is retracted to its full extent, the clutch will slip and thereby prevent damage to the handpiece.

In operation of the handpiece 200, the support rod 216 is extended either manually or by operating the drive of the handpiece 202 in reverse while holding or otherwise maintaining the support rod 216 stationary. Once the support rod 216 has been extended, the handpiece 200 is positioned with the support rod 216 resting on a tooth 232 and with the file 214 positioned to enter a root canal 234 to be cleaned and enlarged as shown in FIG. 10. After positioning the handpiece, the handpiece drive 207 is activated which causes the file 214 to be rotated at a predetermined speed in the range of from about 30 to about 3000 rpm and the support 216 to be retracted whereby the file 214 is advanced in the root canal 234 at a rate in the range of from 0.001 to 0.1 millimeters per revolution of the file 214. In using the handpiece 200 or the handpieces 10 and 100 described above, when the first endodontic file is fully inserted in the root canal and has partially cleaned and enlarged the root canal, the drive of the handpiece is stopped, the file is replaced with the next larger size file and the above described procedure is repeated whereby the endodontic file is advanced into the root canal at a controlled rate and excessive loading of the file does not occur. Additional larger files are successively utilized until the root canal is fully cleaned and enlarged whereby it can be filled with a hardenable composition such as gutta percha.

As will now be understood by those skilled in the art, the improved handpiece of the present invention can include various combinations of apparatus which utilize various control techniques, etc. However, in whatever form the apparatus takes, it includes a rotary drive which rotates a chuck for holding and rotating an endodontic file, and a retractable support rod is positioned adjacent and substantially parallel to the endodontic file. The support rod which can itself take various forms is adapted to rest on a tooth whereby its retraction controls the advance of the endodontic file into a root canal to be cleaned and enlarged. Apparatus is attached to the handpiece for controlling the retraction of the support rod and the advance of the rotating endodontic file at a controlled rate whereby the endodontic file does not self thread into the canal or otherwise become excessively loaded while the root canal is being cleaned and enlarged.

In carrying out the methods of this invention utilizing the improved handpiece of this invention, an endodontic file is first connected to the rotatable chuck of the handpiece. The handpiece is placed with the endodontic file positioned to enter a root canal of a tooth and with the movable support rod of the handpiece resting on a tooth. The endodontic file is rotated at a speed sufficient to clean and enlarge the root canal when the file is advanced into the root canal, and the support rod is moved whereby the endodontic file is advanced into the root canal at a controlled rate so that the endodontic file does not become excessively loaded while the root canal is being cleaned and enlarged.

The present invention, therefore, is well adapted to meet the needs recited above and to carry out the objects and attain the ends and advantages mentioned as well as those inherent therein. While numerous changes can be made in the construction and arrangement of parts, such changes are encompassed within the spirit of this invention as defined by the appended claims.

What is claimed is:

1. In a rotary handpiece for cleaning and enlarging a root canal of a tooth having a rotary endodontic file, said handpiece having a rotary drive which rotates a chuck for holding and rotating the endodontic file, the improvement which comprises:

a retractable support rod attached to and extending from said handpiece positioned adjacent and substantially parallel to said endodontic file and adapted to rest on a tooth whereby the retraction of said support rod controls the advance of said endodontic file into said root canal; and means attached to said handpiece and to said support rod for retracting said support rod and advancing said endodontic file at a controlled rate into said root canal whereby said endodontic file does not become excessively loaded while said root canal is being cleaned and enlarged.

2. The handpiece of claim 1 wherein said means for retracting said support rod comprise:

said support rod including external threads formed thereon;

said handpiece including a rotary member journaled thereto having a threaded bore therein engaging said threaded support rod; and gear means connected to said rotary member and to a rotary drive for rotating said rotary member.

3. The handpiece of claim 2 wherein said rotary drive connected to said gear means is said rotary drive which rotates said chuck.

4. The handpiece of claim 3 wherein said support rod is hollow and said endodontic file is positioned within and extends through said support rod.

5. The handpiece of claim 2 wherein said rotary drive connected to said gear means is a second independent rotary drive from said rotary drive which rotates said chuck.

6. The handpiece of claim 5 wherein the operation of said second independent rotary drive is controlled by an electronic control device.

7. The handpiece of claim 2 which further comprises means attached to said handpiece for selectively reversing the direction of rotation of said rotary member threadedly engaging said support rod.

8. The handpiece of claim 1 wherein said controlled rate at which said support rod is retracted and said endodontic file is advanced is a rate in the range of from about 0.001 to about 0.1 millimeters per revolution of said endodontic file.

9. In a rotary handpiece for cleaning and enlarging a root canal of a tooth having a rotary endodontic file, said handpiece having a rotary drive which rotates a chuck for holding and rotating the endodontic file, the improvement which comprises:

a retractable threaded support rod connected to said handpiece at one end and positioned substantially parallel to said endodontic file, the other end of said support rod being adapted to rest on a tooth whereby the retraction rate of said support rod controls the advance of said endodontic file into said root canal;

a rotary member journaled to said handpiece having a threaded bore therein engaging said threaded support rod whereby the rotation of said rotary member retracts or extends said support rod; and gear means connected to said rotary member and to a rotary drive for rotating said rotary member whereby after being extended, said support rod can be retracted and said endodontic file advanced into said root canal at a controlled rate so that said endodontic file does not become excessively loaded while said root canal is being cleaned and enlarged.

10. The handpiece of claim 9 wherein said rotary drive connected to said gear means is said rotary drive which rotates said chuck.

11. The handpiece of claim 9 wherein said rotary drive connected to said gear means is a second independent rotary drive from said rotary drive which rotates said chuck.

12. The handpiece of claim 9 wherein said support rod is hollow and said endodontic file is positioned within and extends through said support rod.

13. The handpiece of claim 9 which further comprises means attached to said handpiece for selectively reversing the direction of rotation of said rotary member threadedly engaging said support rod.

14. A method of cleaning and enlarging the root canal of a tooth utilizing a rotary endodontic file comprising the steps of:

(a) connecting said endodontic file to a handpiece having a retractable support rod connected thereto at one end and positioned substantially parallel to said endodontic file, the other end of said support rod being adapted to rest on a tooth whereby the retraction rate of said support rod controls the advance of said endodontic file into said root canal;

(b) positioning said handpiece with said endodontic file positioned to enter said root canal and said support rod resting on a tooth;

(c) rotating said endodontic file at a speed sufficient to clean and enlarge said root canal when said file is advanced into said root canal; and (d) retracting said support rod and advancing said rotating endodontic file into said root canal at a controlled rate whereby said endodontic file does not become excessively loaded while said root canal is being cleaned and enlarged.

15. The method of claim 14 wherein said endodontic file is rotated by a rotary drive.

16. The method of claim 14 wherein said support rod is retracted by a second independent rotary drive.

17. The method of claim 16 wherein the operation of said second independent rotary drive is controlled by an electronic control device.

18. The method of claim 14 wherein said support rod is hollow and said endodontic file is positioned within and extends through said support rod.

19. The method of claim 14 which further comprises means attached to said handpiece for selectively reversing the direction of movement of said support rod.

20. The method of claim 14 wherein said controlled rate at which said support rod is retracted and said endodontic file is advanced is a rate in the range of from about 0.001 to about 0.1 millimeters per revolution of said endodontic file.

* * * * *